(12) United States Patent
Cheung

(10) Patent No.: US 10,307,086 B2
(45) Date of Patent: Jun. 4, 2019

(54) GAIT MEASUREMENT WITH 3-AXES ACCELEROMETER/GYRO IN MOBILE DEVICES

(71) Applicant: Hong Kong Baptist University, Hong Kong (HK)

(72) Inventor: Jeffrey Tai Kin Cheung, Hong Kong (HK)

(73) Assignee: HONG KONG BAPTIST UNIVERSITY, Hong Kong (HK)

( * ) Notice: Subject to any disclaimer, the term of this patent is extended or adjusted under 35 U.S.C. 154(b) by 319 days.

(21) Appl. No.: 14/622,933

(22) Filed: Feb. 16, 2015

(65) Prior Publication Data
US 2015/0230734 A1 Aug. 20, 2015

Related U.S. Application Data

(60) Provisional application No. 61/940,801, filed on Feb. 17, 2014.

(51) Int. Cl.
*A61B 5/11* (2006.01)
*A61B 5/00* (2006.01)
*G01P 15/00* (2006.01)

(52) U.S. Cl.
CPC .......... *A61B 5/112* (2013.01); *A61B 5/1123* (2013.01); *A61B 5/7235* (2013.01); *G01P 15/00* (2013.01); *A61B 2562/0219* (2013.01)

(58) Field of Classification Search
CPC ............... A61B 5/112; A61B 5/7235; A61B 2562/0219; G01P 15/00
USPC ................................................. 702/141
See application file for complete search history.

(56) References Cited

U.S. PATENT DOCUMENTS

| | | | | |
|---|---|---|---|---|
| 2002/0013686 A1* | 1/2002 | Bellora | ............ | B60R 21/04 703/8 |
| 2008/0103545 A1* | 5/2008 | Bolea | ............ | A61N 1/0556 607/42 |
| 2010/0271187 A1* | 10/2010 | Uysal | ............ | G06K 7/0008 340/10.4 |
| 2011/0208444 A1* | 8/2011 | Solinsky | ........... | A61B 5/112 702/41 |
| 2012/0016641 A1* | 1/2012 | Raffa | ............ | G06F 1/1694 703/2 |
| 2015/0036138 A1* | 2/2015 | Watson | .......... | G01N 21/31 356/402 |
| 2015/0301167 A1* | 10/2015 | Sentelle | ......... | A61B 5/0205 342/22 |
| 2016/0084869 A1* | 3/2016 | Yuen | ............ | G01P 7/00 73/510 |

OTHER PUBLICATIONS

European Search Report of EP2015748573 dated Sep. 18, 2017.
(Continued)

*Primary Examiner* — Long K Tran
(74) *Attorney, Agent, or Firm* — Shun Yao; Park, Vaughan, Fleming & Dowler LLP

(57) ABSTRACT

The present invention relates to a method of gait measurement using tri-axial accelerometer/gyro in mobile devices. In particular, the present invention relates to a method of gait measurement using tri-axial accelerometer/gyro in mobile devices for monitoring and improving the physical movement of a moving subject.

15 Claims, 21 Drawing Sheets

(56) References Cited

OTHER PUBLICATIONS

Carlijn V. Bouten et. al, Assessment of energy expenditure for physical activity using a triaxial acceleromrter, Medicine and Science in Sports and Exercise, vol. 26, No. 12, 1994, p. 1516-1523.
Barthelemy Ines et. al, Gait analysis using accelerometry in dystrophin-deficient dogs, Neuromuscular Disorders, vol. 19, No. 11, 2009, p. 788-796.
Andre Meichtry et. al, Criterion validity of 3D trunk accelerations to assess external work and power in able-bodied gait, Gait & Posture, vol. 25, No. 1, 2007, p. 25-32.
Jan H. Waarsing et. al, Quantifying the stability of walking using accelerometers, Engineering in Medicine and Biology Society, 1996. Bridging Disciplines for Biomedicine. Proceedings of the 18th Annual International Conference of the IEEE, Amsterdam, p. 469-470.

\* cited by examiner

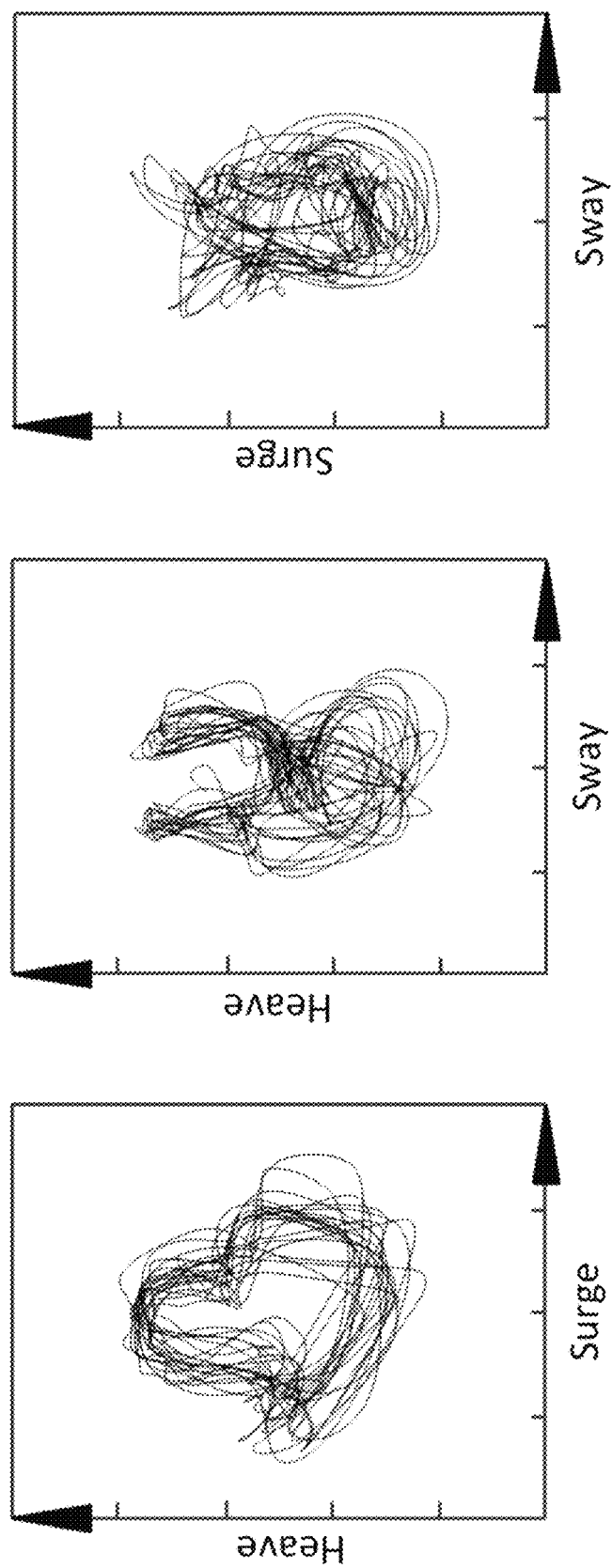

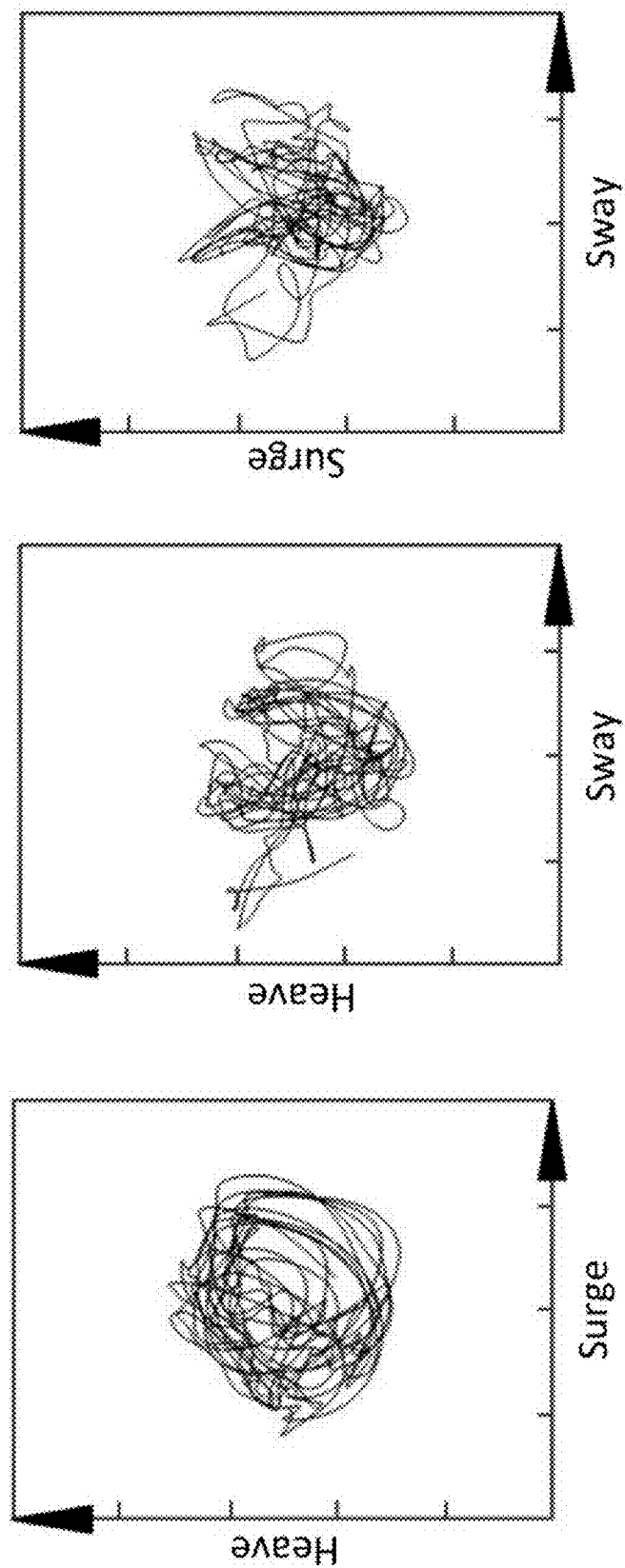

GAIT MEASUREMENT WITH 3-AXES ACCELEROMETER/GYRO IN MOBILE DEVICES

CROSS-REFERENCE TO RELATED APPLICATIONS

This application claims the benefit of U.S. Provisional Patent Application Ser. No. 61/940,801 filed on Feb. 17, 2014, which is hereby incorporated by reference in its entirety.

FIELD OF THE INVENTION

The present invention relates to a method of gait measurement using tri-axial accelerometer/gyro in mobile devices. In particular, the present invention relates to a method of gait measurement using tri-axial accelerometer/gyro in mobile devices for monitoring and improving the physical movement of a moving subject.

BACKGROUND OF THE INVENTION

Gait analysis (the study of walking and running forms) is the key to the study of biomechanics. It is used to monitor and improve body coordination and movement as well as for biometric identification. Traditional gait analysis uses an elaborate optoelectronic setup with multiple Light Emitting Diodes (LEDs) and reflective markers placed on various parts of the subject's body. High-speed cameras are used to capture sequential frames. Due to the cumbersome setup, data are not transmitted wirelessly and the measurement must be conducted in a controlled laboratory environment that not only limits more realistic scenario but also may have an effect on having the subject performing physical movements in a less than natural stance. Useful information is extracted with frame by frame analysis followed by complex algorithms only after the measurement is completed. It is an objective of the present invention to provide a simple gait measurement device coupled with a simple data analysis algorithm. The measurement is not confined to environment with the elaborate setting. It can be carried out under any circumstance and for all types of physical activities. The analysis can be made in a matter of a few seconds to reveal both graphic presentation of gait and postural form in all three motion axes as well as quantitative data known as Dynamic Instability Index (DII) that is a measure of power level exerted by the subject to keep balance while moving. The combined information has a wide range of application in many areas.

Citation or identification of any reference in this section or any other section of this application shall not be construed as an admission that such reference is available as prior art for the present application.

SUMMARY OF THE INVENTION

Accordingly, it is an object of the present invention to provide a method of gait measurement using tri-axial accelerometer/gyro in mobile devices. In particular, the present invention relates to a method of gait measurement using tri-axial accelerometer/gyro in mobile devices for monitoring and improving the physical movement of a moving subject. In a first aspect of the present invention, there is provided a simple data analysis algorithm for gait measurement and diagnosis.

In a second aspect of the present invention there is provided a method for characterizing the movement of a subject comprising the use of a tri-axial accelerometer to formulate: a signature based on measurements of walking, heaving and lateral movements of said subject; and a quantitative indicator indicating the power level dispensed by said subject to keep balance during said motion.

In a first embodiment of the second aspect of the present invention there is provided the method for characterizing the movement of a subject wherein the tri-axial accelerometer is located at the center of gravity of said subject.

In a second embodiment of the second aspect of the present invention there is provided the method for characterizing the movement of a subject wherein said subject can be a human or an animal.

In a third embodiment of the second aspect of the present invention there is provided the method for characterizing the movement of a subject wherein said signature is used in monitoring, diagnosing and improving the movement performance of said subject.

In a fourth embodiment of the second aspect of the present invention there is provided the method for characterizing the movement of a subject wherein said signature is used in monitoring the progress of physical rehabilitation and/or physical well-being of said subject via the movement of said subject.

In a fifth embodiment of the second aspect of the present invention there is provided the method for characterizing the movement of a subject wherein said signature is used in the design and/or fitting of prosthesis for said subject.

In a sixth embodiment of the second aspect of the present invention there is provided the method for characterizing the movement of a subject wherein said signature is used as a biometric identifier of said subject.

In a seventh embodiment of the second aspect of the present invention there is provided the method for characterizing the movement of a subject wherein said signature is used as an indicator for physical impairment analysis of said subject, including but not limited to the diagnosis of kinesthetic problems for animals.

In an eighth embodiment of the second aspect of the present invention there is provided the method for characterizing the movement of a subject wherein said signature is used as an identifier for selecting subjects with better form of movement.

In a ninth embodiment of the second aspect of the present invention there is provided the method for characterizing the movement of a subject wherein said signature is used in design of footwear for said subject.

In a tenth embodiment of the second aspect of the present invention there is provided the method for characterizing the movement of a subject wherein said signature is used as an indicator in the fitting and selection of footwear for said subject.

In an eleventh embodiment of the second aspect of the present invention there is provided the method for characterizing the movement of a subject wherein said signature is used in the design of exercise equipment for said subject.

In a twelfth embodiment of the second aspect of the present invention there is provided the method for characterizing the movement of a subject wherein said signature is used in the design of backpacks and other forms of carry luggage for said subject.

In a thirteenth embodiment of the second aspect of the present invention there is provided the method for characterizing the movement of a subject wherein said method is implemented in software.

In a fourteenth embodiment of the second aspect of the present invention there is provided the method for characterizing the movement of a subject wherein said method is implemented in hardware.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which:

FIG. 8c shows the WHLS of the same subject as in FIG. 8a walking without shoes, the DII being 617;

FIG. 9a shows the WHLS of a 40-year-old female in flat heel shoes, the DII being 246;

DETAILED DESCRIPTION OF THE INVENTION

Figure 1:
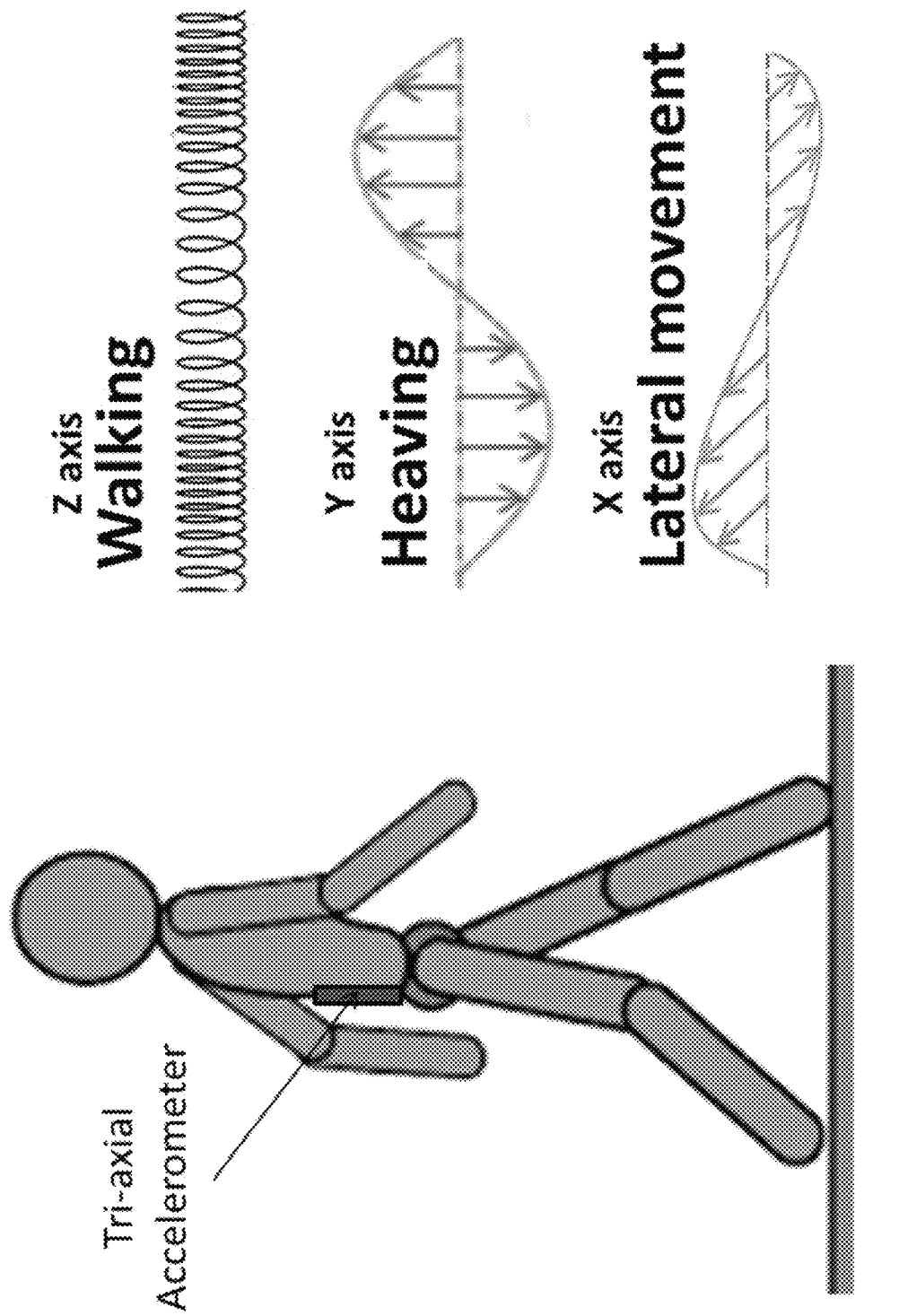
FIG. 1 shows the placement of the device on human during measurement and the three waveforms associated with the motion.

The present invention is not to be limited in scope by any of the specific embodiments described herein. The following embodiments are presented for exemplification only.

In a first aspect of the present invention, there is provided a simple data analysis algorithm for gait measurement and diagnosis.

In a second aspect of the present invention there is provided a method for characterizing the movement of a subject comprising the use of a tri-axial accelerometer to formulate: a signature based on measurements of walking, heaving and lateral movements of said subject; and a quantitative indicator indicating the power level dispensed by said subject to keep balance during said motion.

In a first embodiment of the second aspect of the present invention there is provided the method for characterizing the movement of a subject wherein the tri-axial accelerometer is located at the center of gravity of said subject.

In a second embodiment of the second aspect of the present invention there is provided the method for characterizing the movement of a subject wherein said subject comprising human and animal.

In a third embodiment of the second aspect of the present invention there is provided the method for characterizing the movement of a subject wherein said signature is used in monitoring, diagnosing and improving the movement performance of said subject.

In a fourth embodiment of the second aspect of the present invention there is provided the method for characterizing the movement of a subject wherein said signature is used in monitoring the progress of physical rehabilitation and/or physical well-being of said subject via the movement of said subject.

In a fifth embodiment of the second aspect of the present invention there is provided the method for characterizing the movement of a subject wherein said signature is used in the design and/or fitting of prosthesis for said subject.

In a sixth embodiment of the second aspect of the present invention there is provided the method for characterizing the movement of a subject wherein said signature is used as biometric identifier of said subject.

In a seventh embodiment of the second aspect of the present invention there is provided the method for characterizing the movement of a subject wherein said signature is used as indicator for physical impairment analysis of said subject, including but not limited to the diagnosis of kinesthetic problems for animals.

In an eighth embodiment of the second aspect of the present invention there is provided the method for characterizing the movement of a subject wherein said signature is used as identifier for selecting subjects with better form of movement.

In a ninth embodiment of the second aspect of the present invention there is provided the method for characterizing the movement of a subject wherein said signature is used in design of footwear for said subject.

In a tenth embodiment of the second aspect of the present invention there is provided the method for characterizing the movement of a subject wherein said signature is used as indicator in the fitting and selection of footwear for said subject.

In an eleventh embodiment of the second aspect of the present invention there is provided the method for characterizing the movement of a subject wherein said signature is used in the design of exercise equipment for said subject.

In a twelfth embodiment of the second aspect of the present invention there is provided the method for characterizing the movement of a subject wherein said signature is used in the design of backpacks and other forms of carry luggage for said subject.

In a thirteenth embodiment of the second aspect of the present invention there is provided the method for characterizing the movement of a subject wherein said method is implemented in software.

In a fourteenth embodiment of the second aspect of the present invention there is provided the method for characterizing the movement of a subject wherein said method is implemented in hardware.

Walking, Heaving, Lateral-Movement Signature (WHLS)

In one embodiment of the present invention there is provided a real-time diagnosis technique with a tri-axial accelerometer embedded in a smart phone or a stand-alone tri-axial accelerator package with power and data acquisition components. In most cases, where the translational motions are dominant, the tri-axial accelerometer data will suffice. However, for more accurate measurement, a tri-axial accelerometer/gyro device should be used to acquire movements in all six degrees of freedom (three translations: sway, surge, heave and three rotations: pitch, roll and yaw). In running or walking, an object moves periodically in all three directions: heave (up/down), sway (side/side) and surge (forward/backward) shown in FIG. 1. Consider the variation of acceleration along these directions, the heave (up/down) and sway (side/side) acceleration act like a transverse wave (i.e. amplitude perpendicular to the movement direction), while the surge (forward/backward) acceleration acts like a longitudinal wave (amplitude parallel to movement direction).

Therefore, the motion of running or walking can be expressed as a linear combination of these three waveforms. Instead of measuring the displacement, a more relevant and direct quantity to measure is the acceleration. During test, the sensor unit will be strap mounted to the center of gravity of the subject. For human body, it will be placed tightly against the center of the lower back. Data collection rate is carried out at 100 Hz. During a set of test, the subject will instructed to carry out physical activities such as walking, running, ascending and descending stairs, etc. for a short period of time of approximately 20 seconds. Data taken during the first and last five seconds will be discarded because they are not at a steady state. Only the data taken under steady state will be used. Each set of data consists of three acceleration values, $a_{1x}$, $a_{1y}$ and $a_{1z}$ shown in FIG. 2, corresponding to the three acceleration components along the respective axes. The magnitude of each component will be plotted in a Cartesian coordinate. This plot is equivalent to plot the time evolving trajectory of the net total acceleration vector in a polar coordinate. It will yield a three dimensional trajectory, named WHLS (Walking, Heaving and Lateral movement Signature). Its shape is unique for each individual. With the sensitivity of tri-axial accelerometer of approximate 0.003 g (g=9.8 m/s$^2$), a 0.001 m resolution limit in displacement within 50 msec time interval can be achieved. The high sensitivity is capable to reveal slight movement anomaly due to the physical condition of the person, such as back pain, weak knees, limp, discomfort in footwear, carrying a load, etc. Embodiments of the present invention have compiled data from various individuals engaged in various physical activities.

Figure 2:
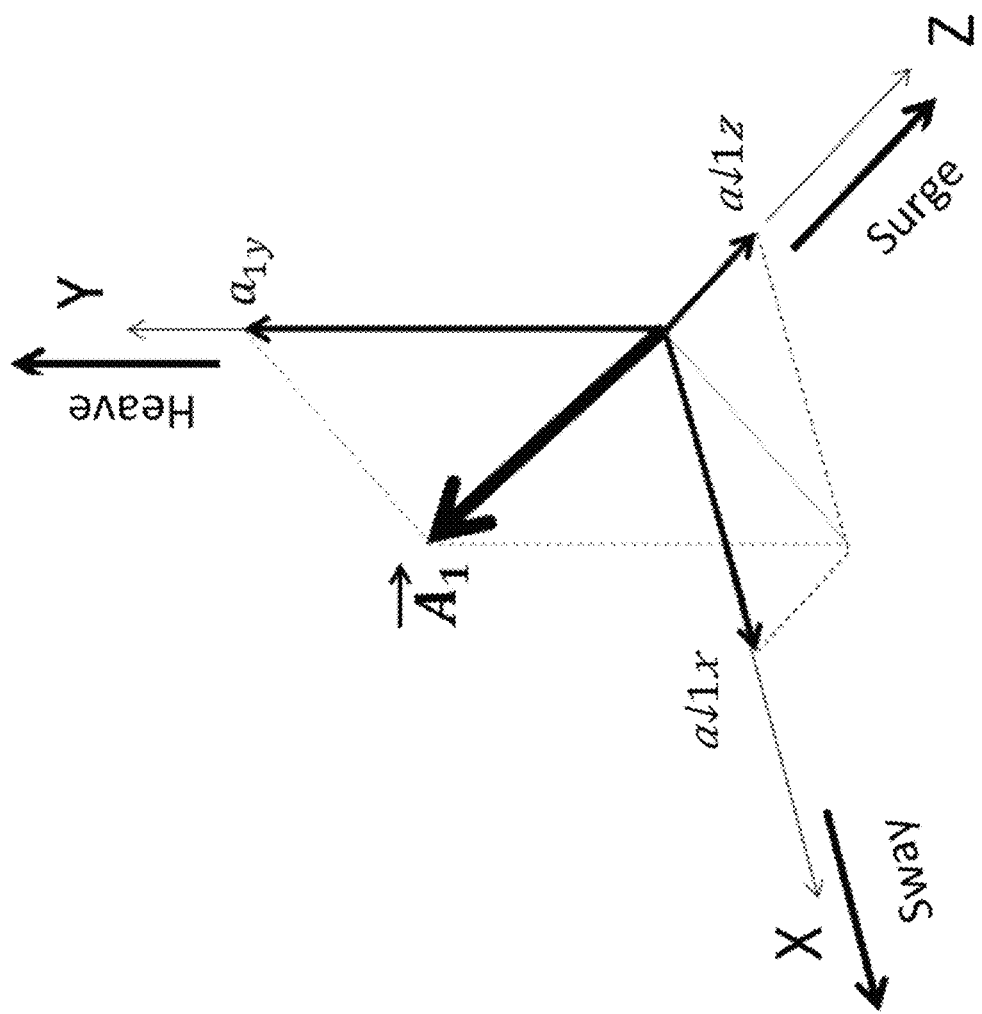
FIG. 2 shows the measured acceleration in a Cartesian coordinate at time $t_1$. The three axes X, Y, Z represent sway, heave and surge movement, respectively.
Figure 3:
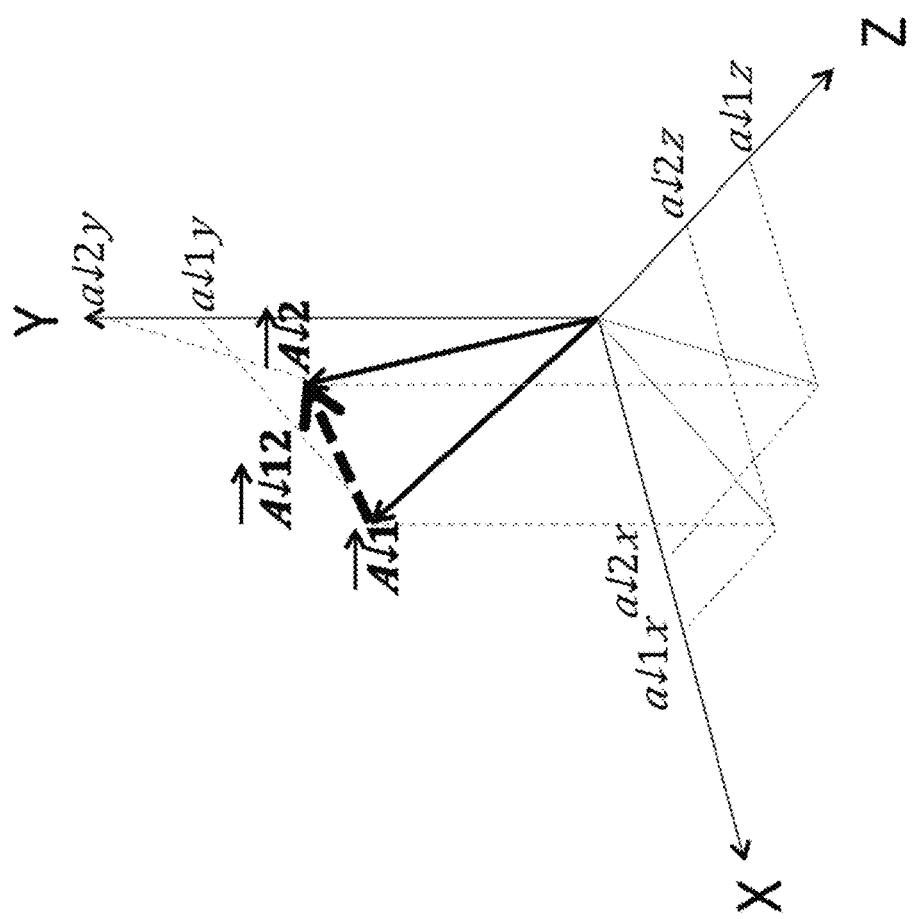
FIG. 3 shows the measured acceleration vector $\vec{A}_2$ at time $t_2$ and its relationship to vector $\vec{A}_{12}$, the vector corresponding to the movement of center of gravity of the test subject.
Figure 4:
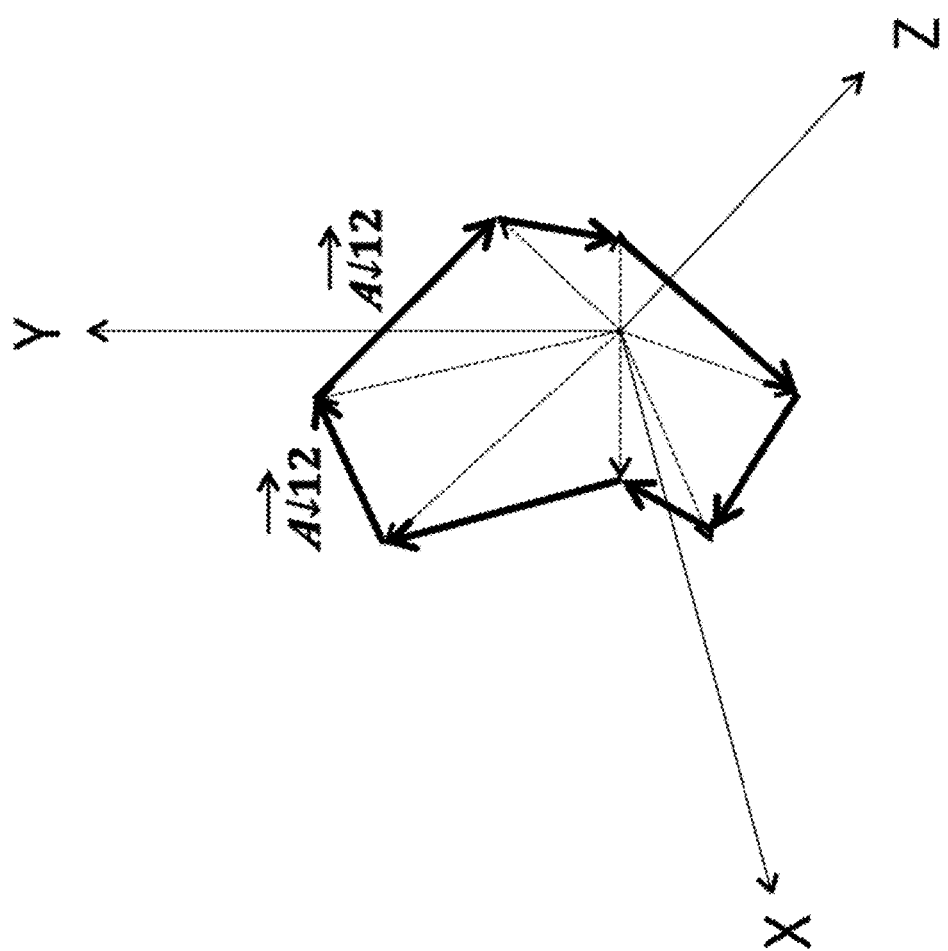
FIG. 4 shows the trace of vectors of the movement of the center of gravity of the test subject.

More precisely as shown in FIG. 2, vector $\vec{A}_1$ is the summation of the three components $a_{1x}$, $a_{1y}$, and $a_{1z}$ taken at time $t_1$. Second set of data acquisition takes place at time point $t_2$ after a time interval $\Delta t_{12}$. The new set of acceleration components is labeled as $a_{2x}$, $a_{2y}$, and $a_{2z}$. The vector sum of these components is vector $\vec{A}_2$, shown in FIG. 3. Therefore, during this time interval, the acceleration vector of the center of gravity of the test subject is $\vec{A}_{12}$, where vectors $\vec{A}_1 + \vec{A}_{12} = \vec{A}_2$. This will continue throughout the movements and the vectors $\vec{A}_{ij}$ will eventually form a continuous trace to represent the trajectory of the center of gravity of the moving test subject in the acceleration coordinate space as shown in FIG. 4. If the subject is moving along a straight line at a constant velocity, the net sum of all vectors of each cycle must equal to zero or $\Sigma_i \vec{A}_i$, according to Newton's Laws of Motion. However, the total acceleration of the movement is of the center of gravity of the subject under test, or $\Sigma \vec{A}_{ij}$, is finite. The result can be used to assess valuable information regarding gait. Data analysis can be divided into two parts: (1) 3D graphic trace of the acceleration trajectory or the Walk Heave Lateral Movement Signature (WHLS) and (2) quantitative results relating to the subject's ability to keep balanced during motion.

Figure 5:
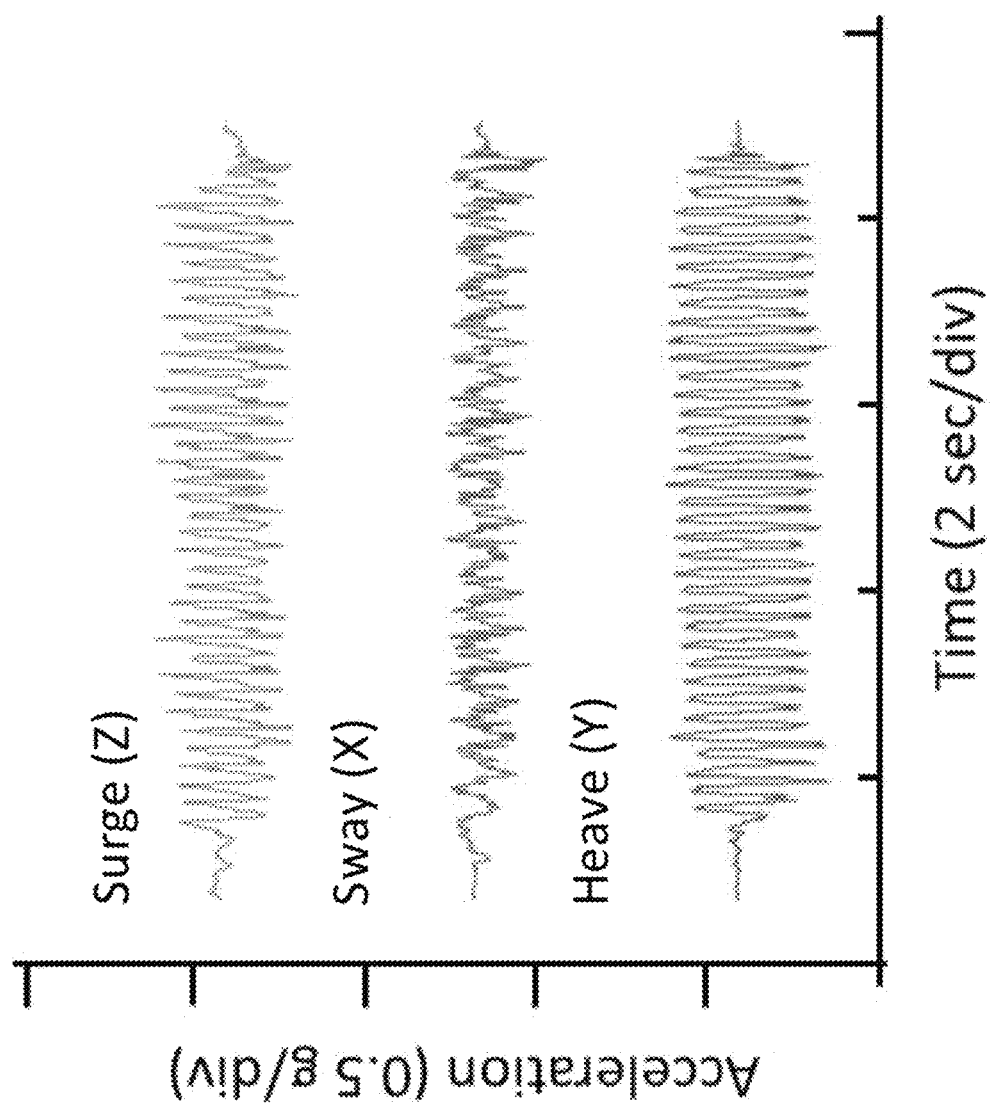
FIG. 5 shows the raw data of measured acceleration along three axes of the test subject.
Figure 6:
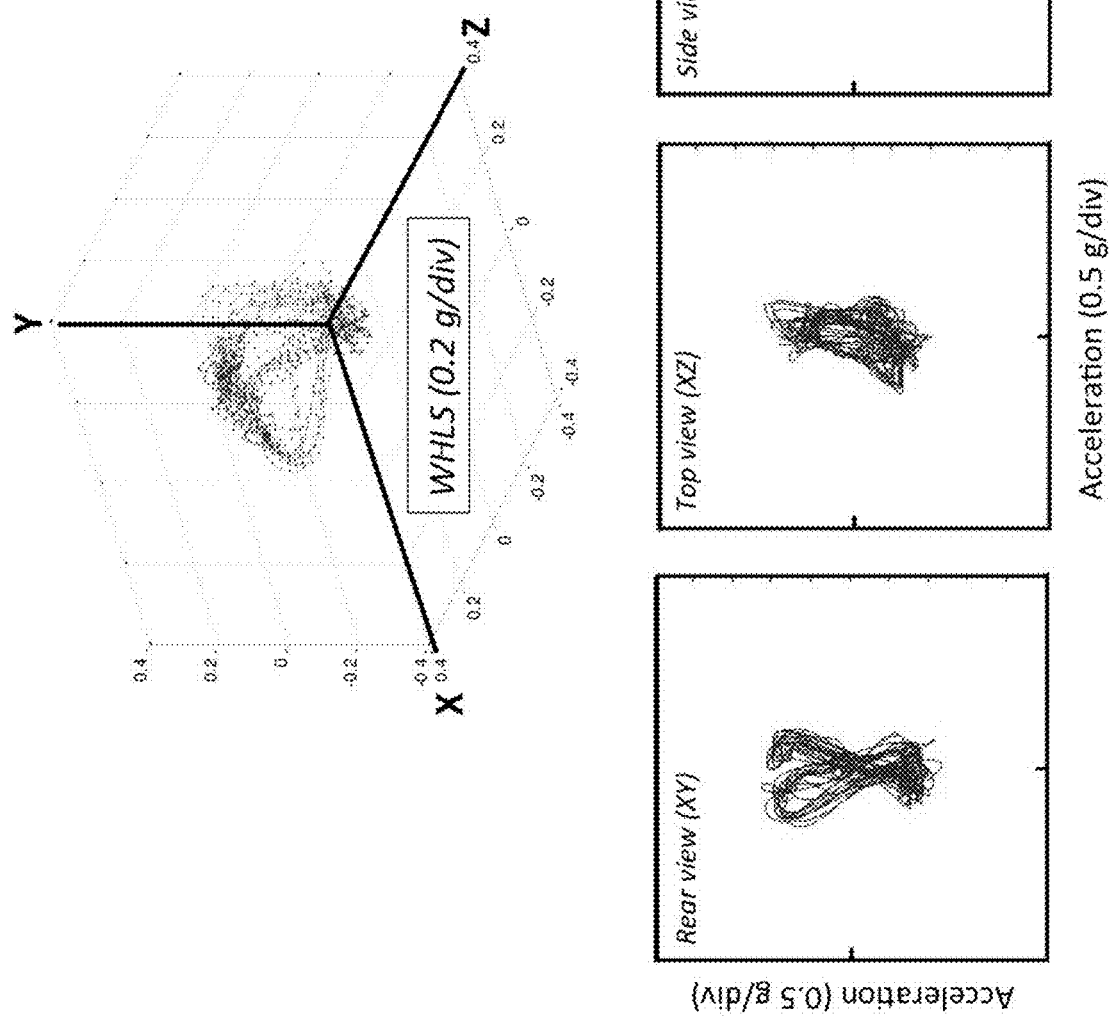
FIG. 6 shows a typical Walking Heaving Lateral-Movement Signature (WHLS) pattern and views from three direction of the test subject.

FIG. 5 shows a plot of the raw acceleration data along 3 axes. The data, when plotted in a 3D polar coordinate, yields a 3D trace of the acceleration vector trace over the period of walking as shown in FIG. 6a. 2D views from three different directions are also shown in FIG. 6b. The pattern is named "Walking Heaving Lateral movement Signature", or WHLS. It is unique for each individual person and for different movement. It can be used for biometric identification and diagnosis of gait imperfection. Traditional gait measurement relies solely on analyzing the amplitude and frequency of periodic movement. The phase relationships between different movements are ignored, thus missing valuable biomechanical information. This approach takes the relative phase difference between periodic movements along three axes into account to unveil a wealth of useful information including small irregular features related to gait.

Following figures show a collection of WHLS patterns of different individuals with same movement (i.e. walking) or same individual in different movements (e.g. normal walking vs. ascending on staircase, with or without bearing a load on the back), or in different foot wears such as heel less shoes, high heels, etc. The uniqueness clearly supports the use of such patterns for biometrics and many other applications.

Important features include the following.

Figure 7A:
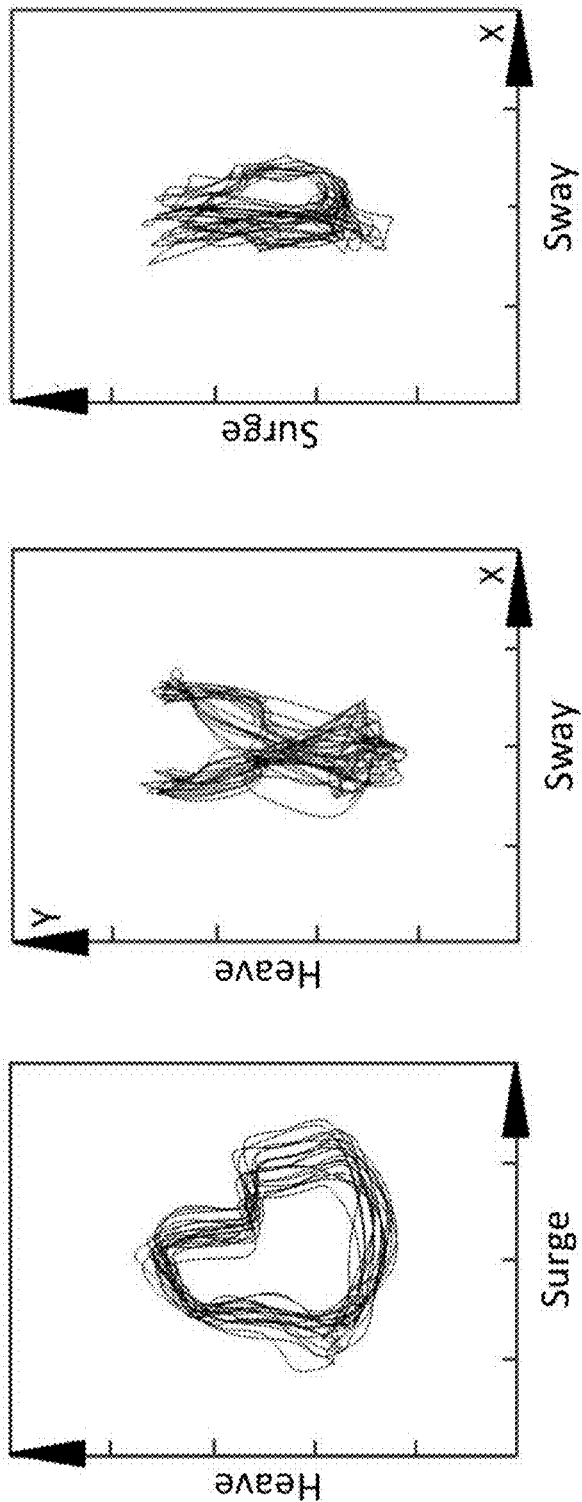
FIG. 7a shows the WHLS of a 27-year-old male, with the Dynamic Instability Index (DII) being 259.
Figure 7A:
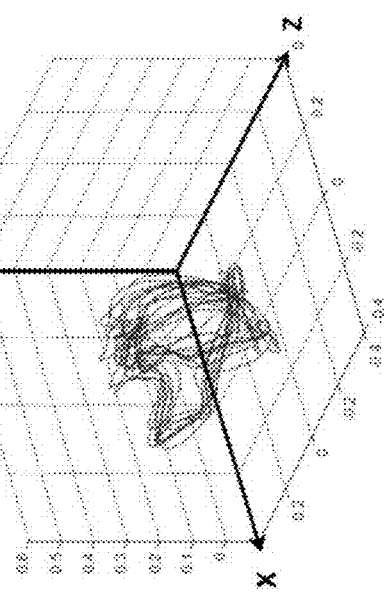
Figure 7B:
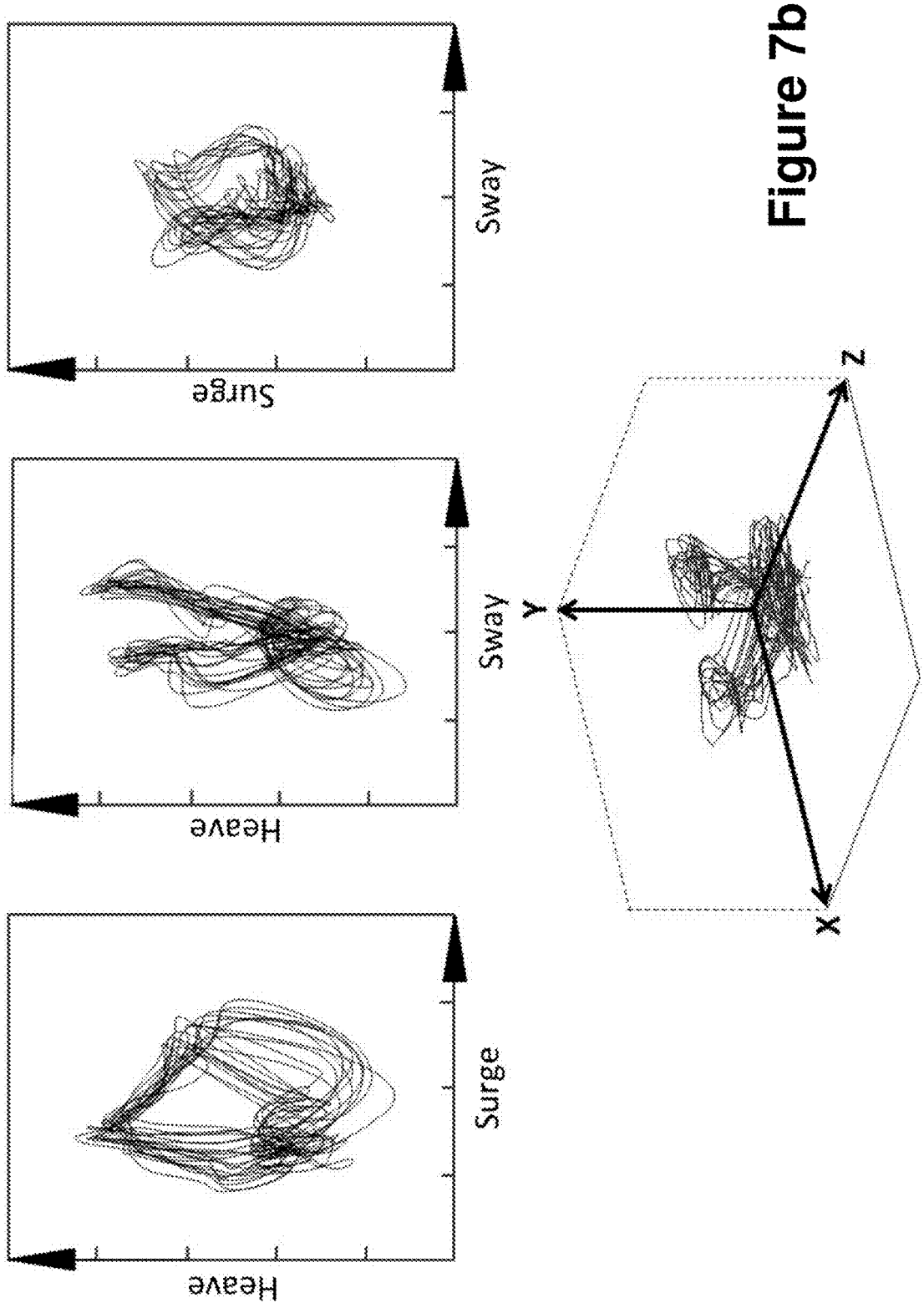
FIG. 7b shows the WHLS of a 68-year-old male, where the DII is 416, and the asymmetry in the YX view is caused by a weak right knee.
Figure 7C:
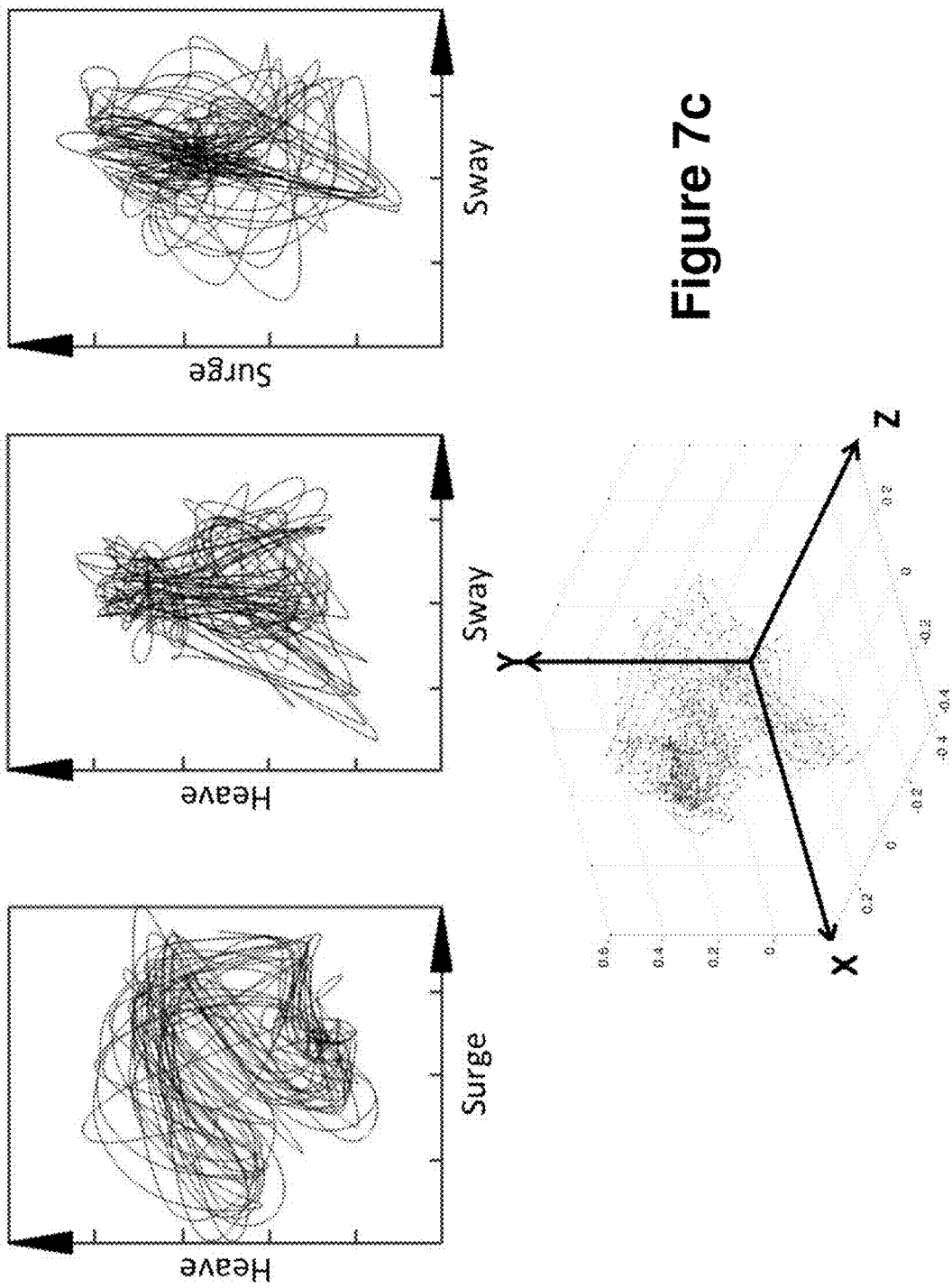
FIG. 7c shows the WHLS of a 23-year-old male, where the DII is 1186, and the test subject had never exercised and had had a case of obesity.

Comparing FIGS. 7a, 7b and 7c:

These three WHLS patterns show the difference between the individuals with difference age and level of physical fitness. The individual in FIG. 7a is a 27-year-old male with a routine regiment of exercise and balanced diet. His physical fitness is reflected in the tight and well-defined WHLS pattern. Another prominent feature is seen in the X/Y (or lateral movement/heave) view that shows nearly symmetric and alternate heave movement in left and right. FIG. 7b shows the WHLS pattern of a 68-year-old male. The pattern is much less well defined. There is clearly asymmetry between left and right movements in particularly in the Y-X plot. The behavior is caused by weak left knee. This subject has been monitored for over 10 months with any noticeable change in this distinctive feature. FIG. 7c shows the WHLS of a 23-year-old male who is completely out of shape and has shown a sign of obesity. The lack of fitness is reflected in the pattern which is loose and ill defined. This group of results suggests the use of WHLS as a simple way to assess one's fitness.

Figure 8A:
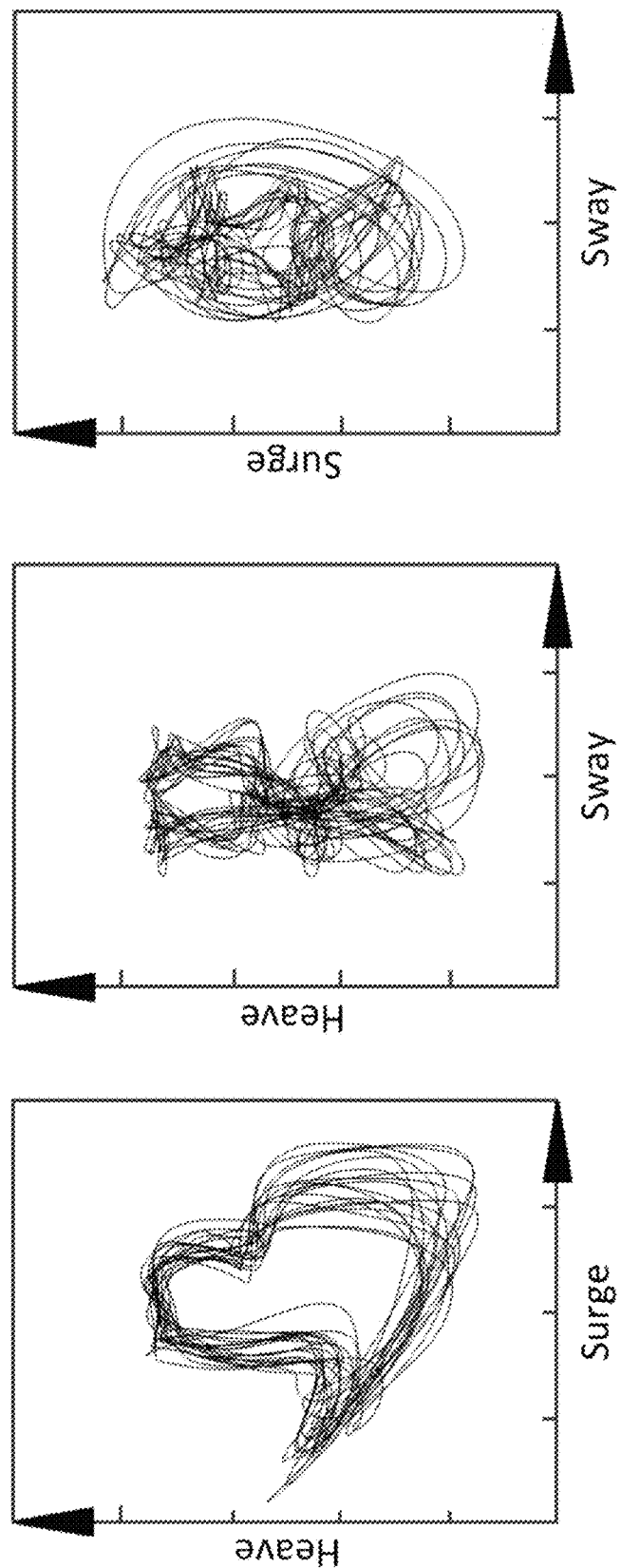
FIG. 8a shows the WHLS of a 24-year-old male with both shoes, the DII being 754.
Figure 8B:
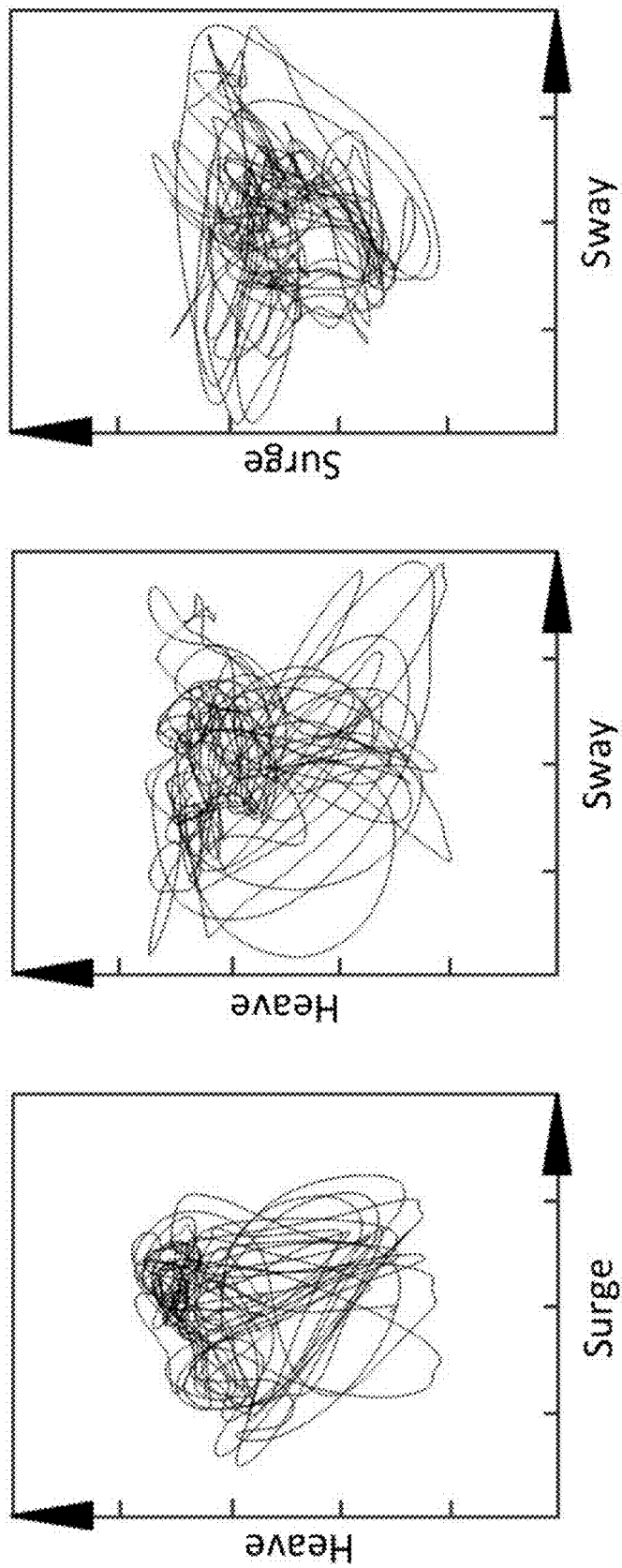
FIG. 8b shows the WHLS of the same subject as in FIG. 8a walking in only one shoe, the DII being 914.

Comparing FIGS. 8a, b, c:

These WHLS patterns depict the same individual under different walking conditions. FIG. 8a represents a 2D WHLS pattern taken under normal walking condition with shoes on both feet. FIG. 8b is the WHLS pattern taken under the same condition except the subject was wearing only one shoe. As a result, this imbalance immediate translates into a chaotic WHLS pattern in which the periodic pattern is no longer recognizable. However, when the same subject was walking with both shoes removed, the balance was largely recovered as well as the WHLS pattern shown in FIG. 8c. The dramatic change shows the high sensitivity of WHLS as a tool to detect any gait imperfection due to discomfort in feet and footwear.

Figure 9B:
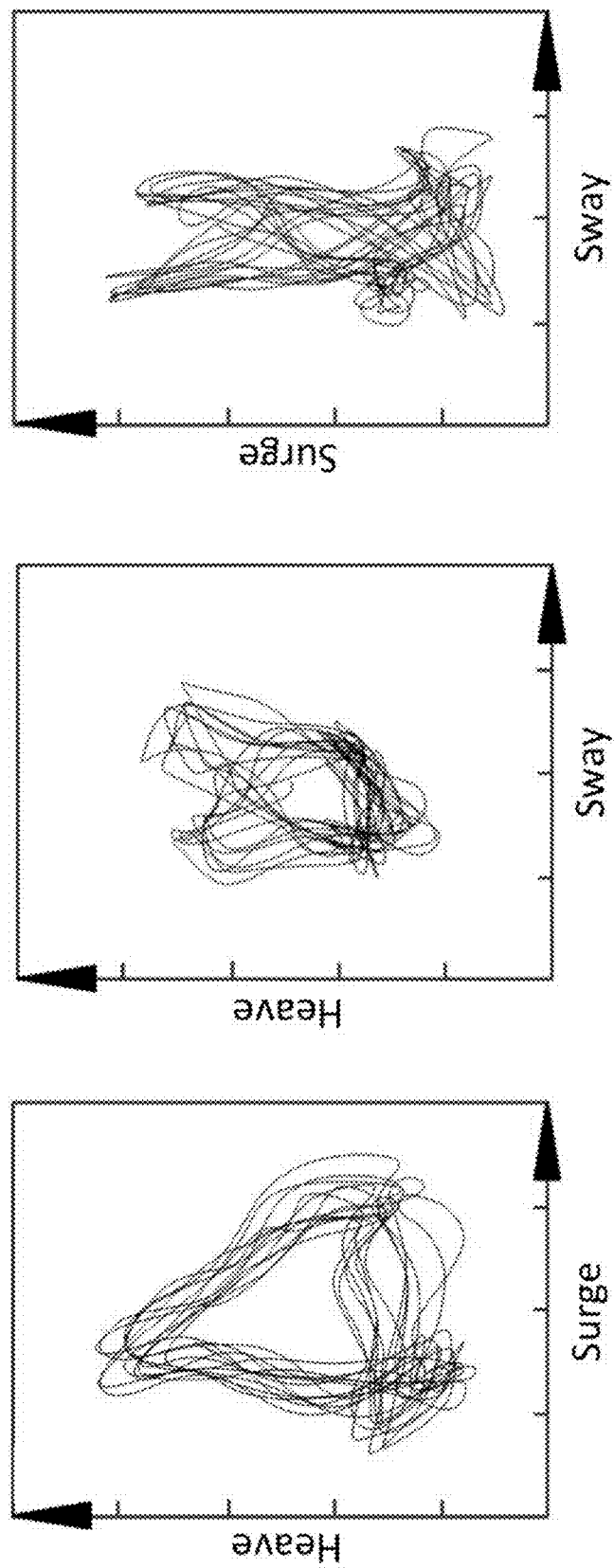
FIG. 9b shows the WHLS of the same subject as in FIG. 9a except wearing 2" high heel shoes, the DII being 567.

Comparing FIGS. 9a, b:

These two WHLS patterns depict a middle-aged lady walking in flat heeled feet (FIG. 7a) and in high heel. This subject wears high heel in rare occasions. Results show a much higher (5 times higher) level of power needed to keep balanced in high heels. It points out the effectiveness of WHLS pattern as an effective way for footwear design.

Figure 10A:
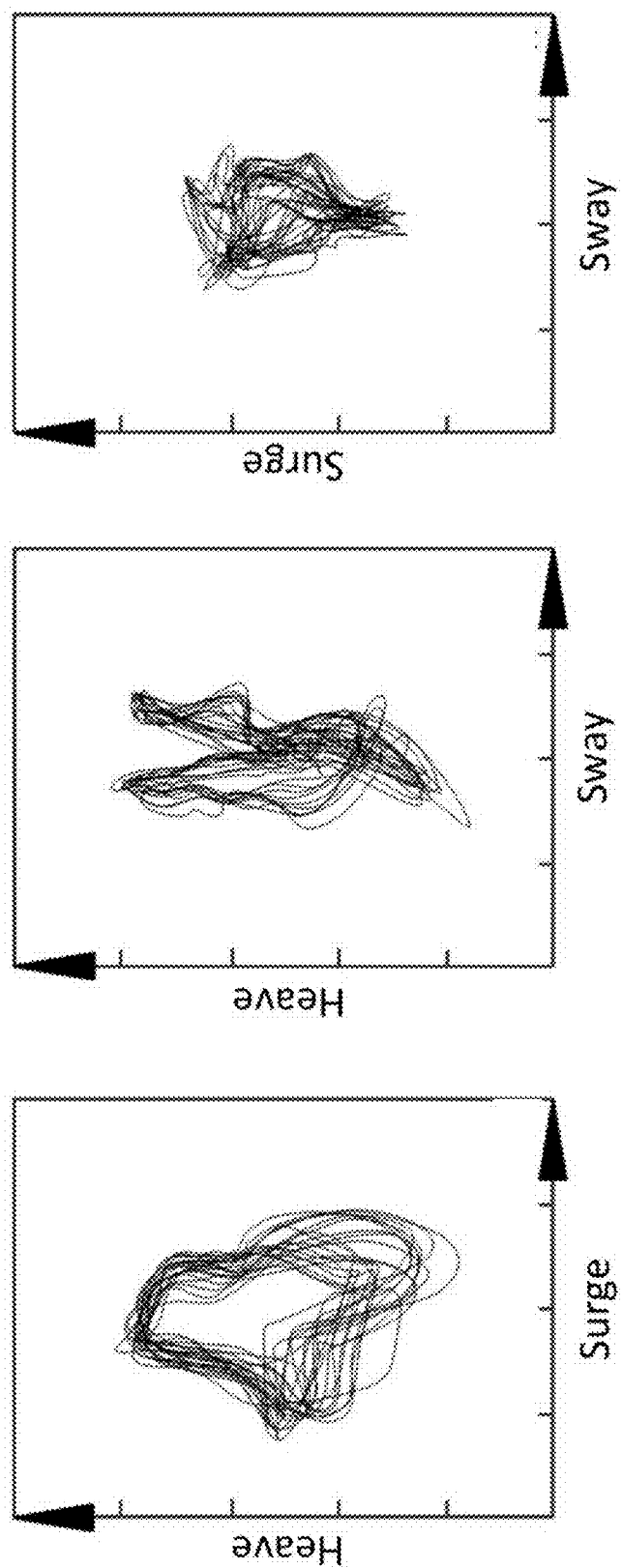
FIG. 10a shows the WHLS of a 24-year-old male carrying a 6 kg backpack on both shoulders; the DII being 355.
Figure 10B:
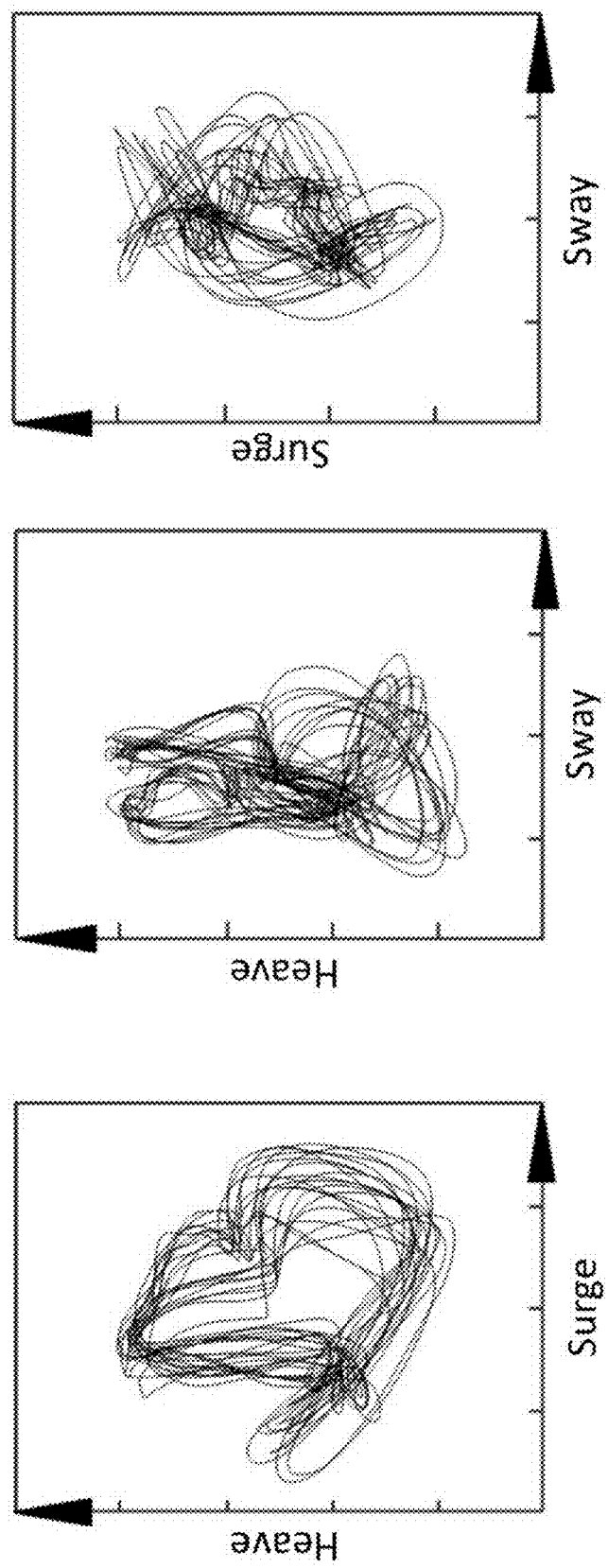
FIG. 10b shows the WHLS of a 24-year-old male carrying a 6 kg backpack with one shoulder; the DII being 796.

Comparing FIGS. 10a, b:

These two figures depict WHLS patterns of a person carrying a backpack with a 6 kg load either carried with both shoulders (FIG. 10a) or slinging across one shoulder (FIG. 10b). The results clear indicate the two shoulders style is more efficient and healthy. This approach can be used to improve backpack design.

Figure 11A:
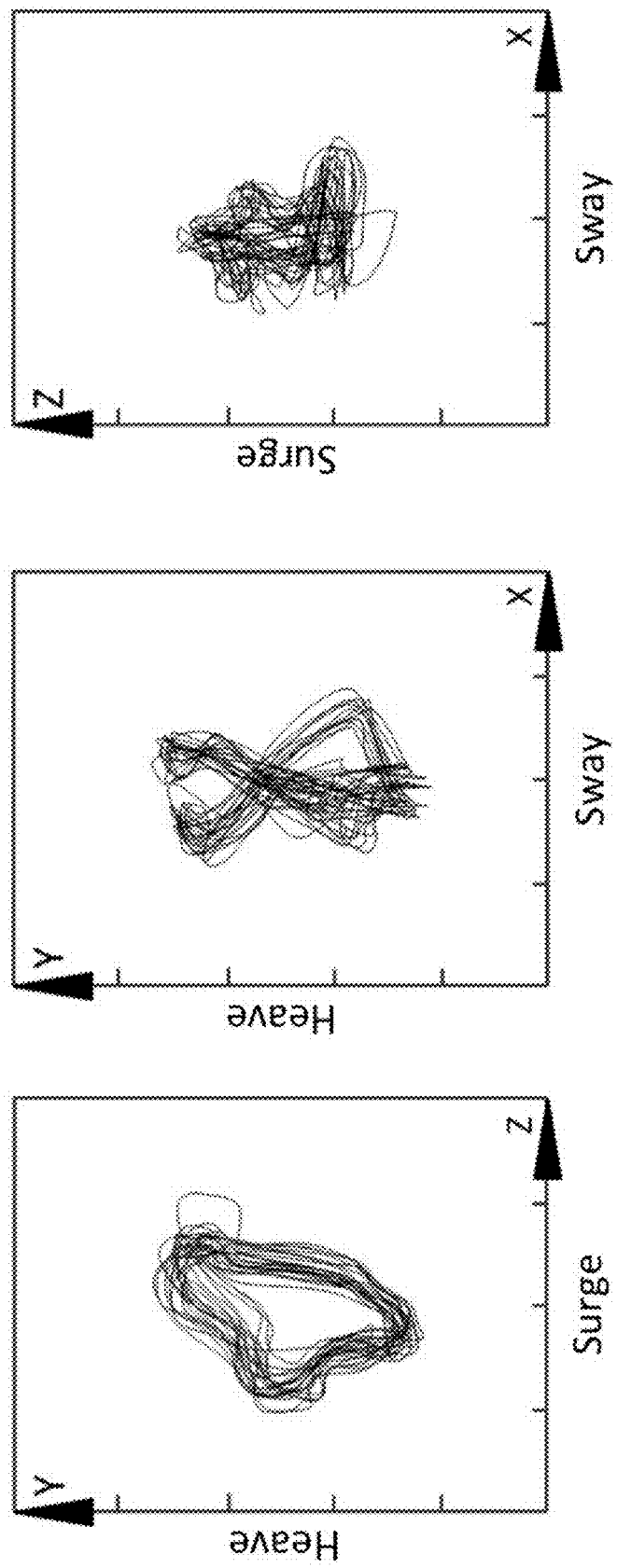
FIG. 11a shows the WHLS of a 24-year-old female walking; the DII being 279.

Comparing FIGS. 11a, b, c

Figure 11B:
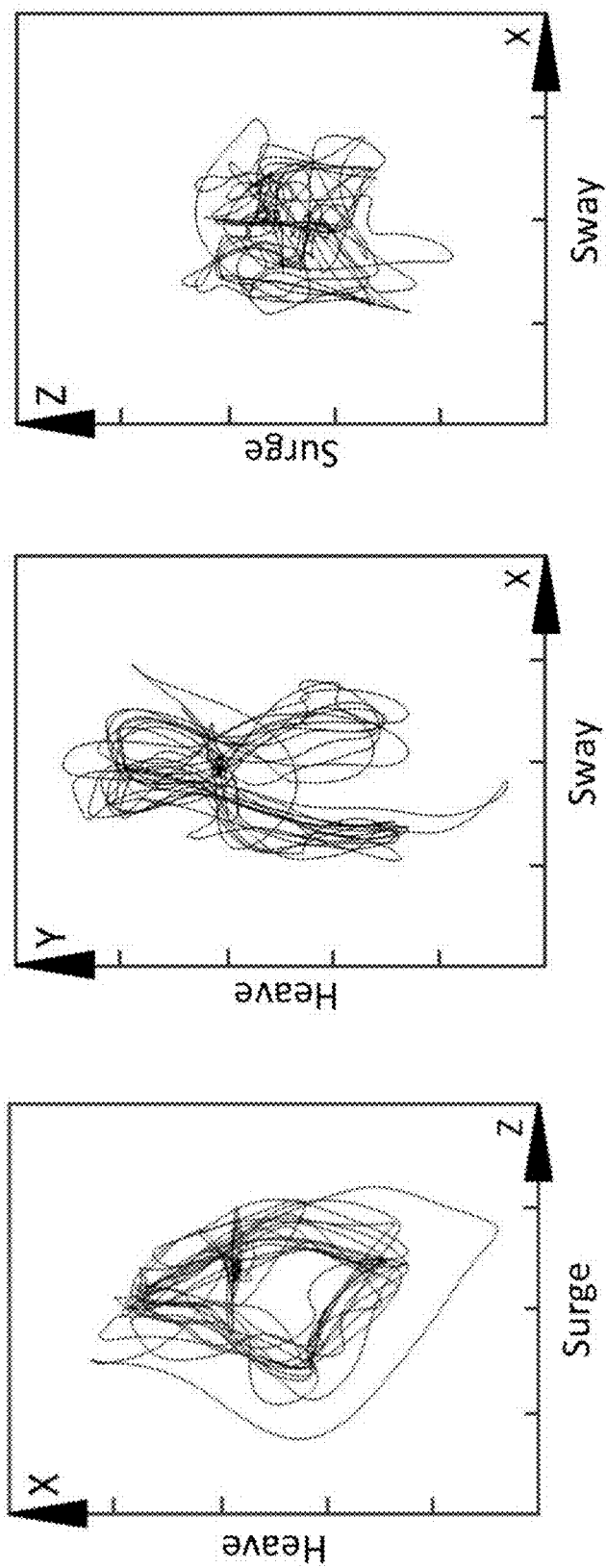
FIG. 11b shows the WHLS of the same subject as FIG. 11a ascending a staircase, the DII being 274.
Figure 11C:
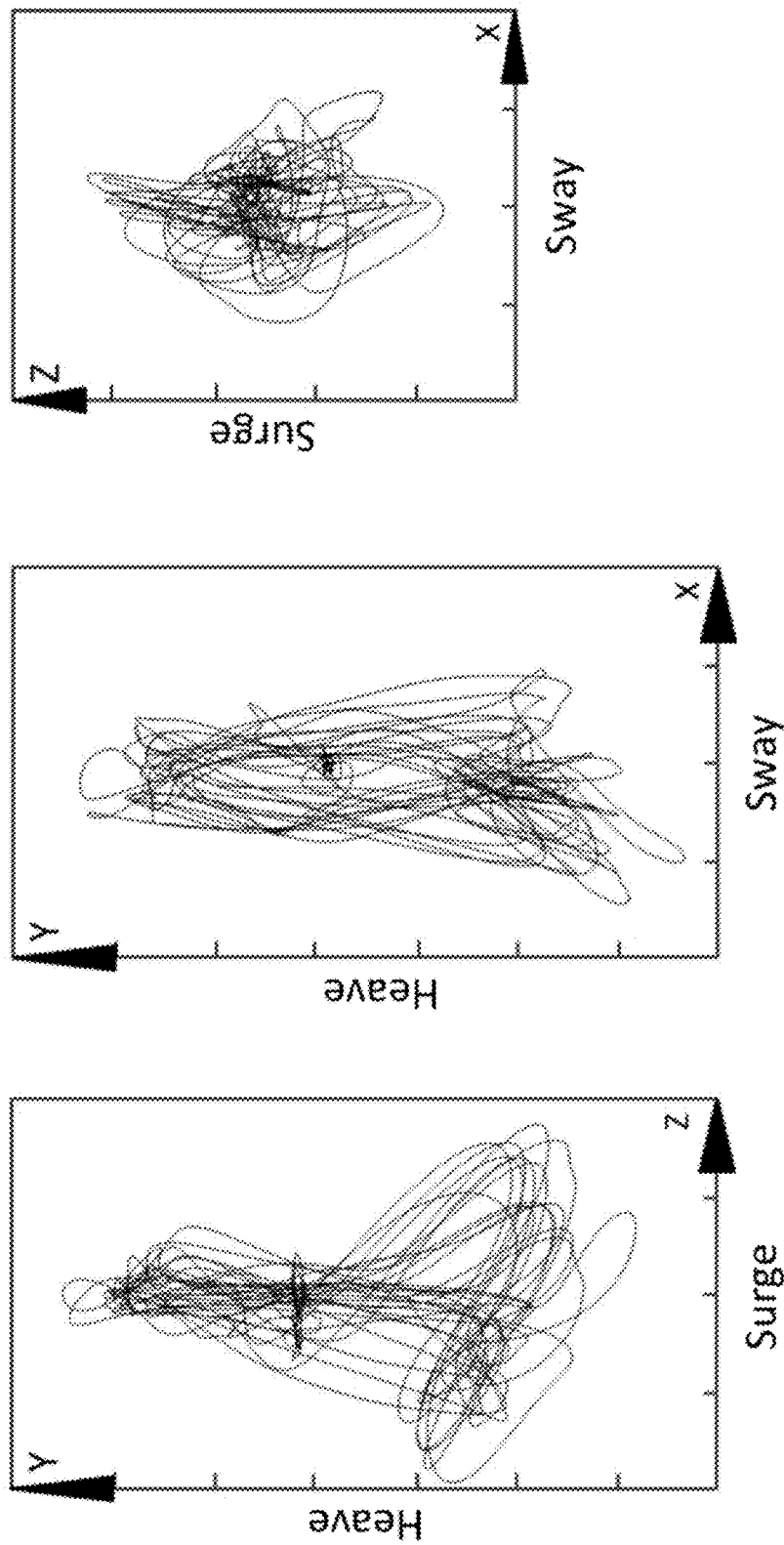
FIG. 11c shows the WHLS of the same subject as FIG. 11a descending from a staircase, the DII being 1501.

These three sets of 2D WHLS patterns systematically compare a person normal walking (FIG. 11a), ascending staircase (FIG. 11b), and descending staircase (FIG. 11c). Results show a distinctive difference between them with the descending movement requiring higher power level to maintain the gait. Another feature worthy to point out is the X/Y view of ascending WHLS. Similar to the normal walking case, it also has two finger-like features corresponding to the periodic leg movement. However, their polarity is opposite as they point downward instead of pointing upward as in normal walking. This is due to the heel/toe action in the normal walking, yet this action is missing in the ascending movement.

Quantitative Analysis of the WHLS Data—Dynamic Instability Index (DII)

To further understand the WHLS patterns, one embodiment of the present invention provides an algorithm to calculate the amount of power level required to maintain the gait. The value that is adjusted to a range between zero and a few thousand for practical purpose is named Dynamic Instability Index (DII). For the same speed, a low DII signals better fitness and a more effective gait. A high DII implies the opposite. This algorithm extracts the power requirement from the WHLS pattern by performing a double integration along the acceleration trajectory.

A Detailed Process Description

For each time interval, the center of gravity of the individual under test proceeds along acceleration vector $\vec{A}_{ij}$. For very short time interval, the acceleration can be assumed to have a linear time dependence, namely, $\vec{A}_{ij}=k_{ij}t$, where $k_{ij}$ is the slope of the vector $\vec{A}_{ij}$ in the acceleration-time space. The slope $k_{ij}$ can be determined from the coordinates of vectors $\vec{A}_i$ and $\vec{A}_j$ as:

$$k_{ij} = \frac{[(a_{xj} - a_{xi})^2 + (a_{yj} - a_{yi})^2 + (a_{zj} - a_{zi})^2]^{\frac{1}{2}}}{\Delta t_{ij}}.$$

The distance $S_{ij}$ that the center of gravity travels during the time interval $\Delta t_{ij}$, which happens to be the reciprocal of the data rate, can be obtained by performing a double integral:

$$S_{ij} = \int\int_{t_i}^{t_j} \vec{A}_{ij}\, dt\, dt = \frac{1}{6}k_{ij}\Delta t_{ij}^3.$$

By substituting $\vec{A}_{ij}=k_{ij}t$ into the double integral of the last equation, the distance can be calculated by $$S_{ij} = \frac{1}{6}k_{ij}\Delta t_{ij}^3.$$

Consequently, the amount of work done during this time can be obtained by $$W_{ij} = F(t)S_{ij} = \frac{F(t)k_{ij}\Delta t_{ij}^3}{6}.$$

For simplicity, due to the short time interval, it is assumed that the force F to be independent of time and simply F=m<a>, where m is the mass and <a> is the average acceleration during the time interval. Therefore, the total work performed or the energy spent during the time can be obtained by taking the summation of forces associated with individual segments along the trajectory. For convenience, one embodiment of the present invention further divides this value by the total measurement time. The result is the power level that is needed to keep the individual under test in balance. In order to make the result in a proper range, this embodiment of the present invention multiply the number by a constant bring the range to about 1000 under normal circumstances. It is named as Dynamic Instability Index (DII). Higher DII indicates higher power level to maintain the gait and is associated with less physical fitness and vice versa. Some representative DIIs for various cases are listed in Table 1 for reference. The calculation time is just a fraction of a second. Its magnitude provides a quantitative measure of the gait quality.

TABLE 1

Some representative DIIs for various cases.

| Figure | Age | Gender | Activity | Fitness level | DII |
|---|---|---|---|---|---|
| 7a | 28 | M | Normal walking | Excellent | 259 |
| 7b | 68 | M | Normal walking | Average | 416 |
| 7c | 23 | M | Normal walking | Poor | 1186 |
| XXX | 22 | M | Normal walking | Poor | 826 |
| XXX | 23 | F | Normal walking | Good | 246 |
| XXX | 54 | M | Normal walking | Average | 426 |
| XXX | 63 | M | Normal walking | Average | 395 |
| 9a | 40 | F | Flat heel | Excellent | 246 |
| 9b | 40 | F | High heel | Excellent | 567 |
| 10a | 24 | M | Load both shoulders | Average | 355 |
| 10b | 24 | M | Load one shoulder | Average | 796 |
| 11b | 23 | F | Ascending stairs | Good | 274 |
| 11c | 23 | F | Descending stairs | Good | 1507 |

The measurement described here use a 100 Hz data rate that proves to be adequate for studying human gait. However, if the gait consists of sudden spikes such as horse galloping, devices with higher data rate must be used. Though the analysis algorithm remains the same.

Figure 12:
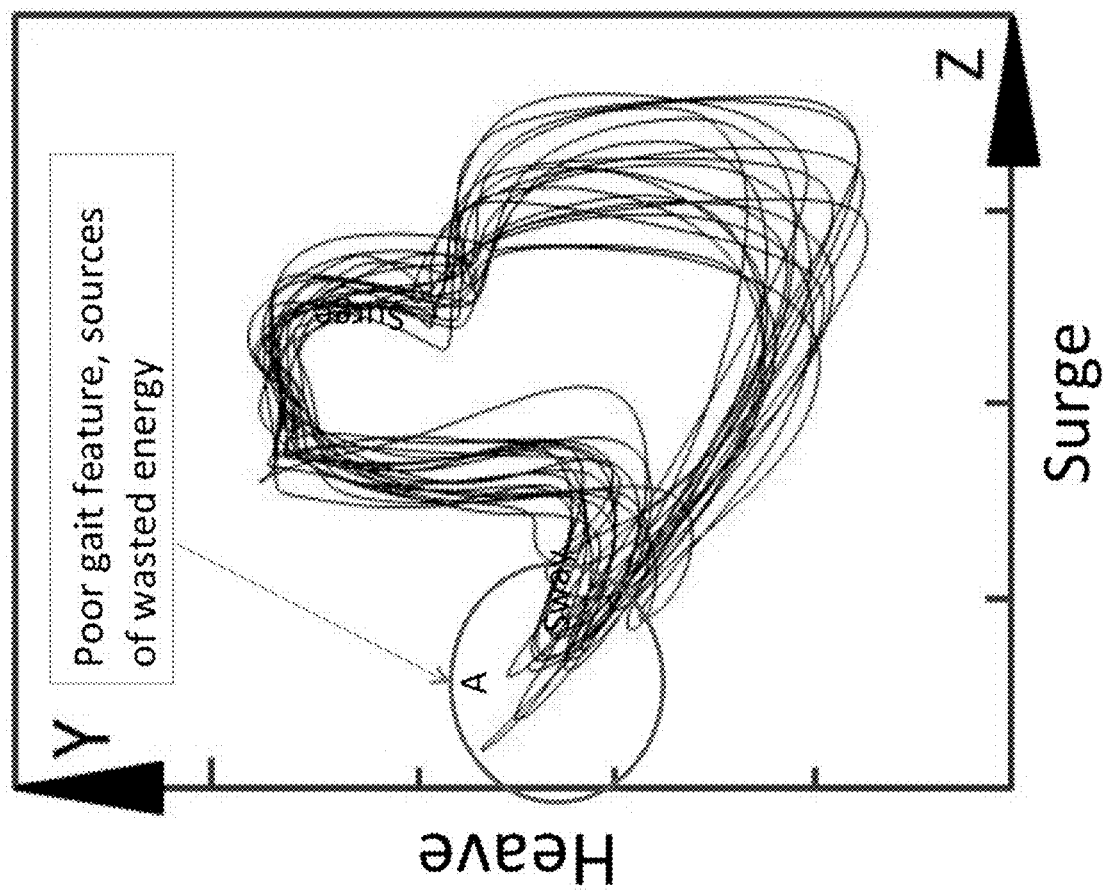
FIG. 12 shows the surge/heave view of the WHLS of a 27-year-old male, where the circled feature indicates wasted movement in gait.

This analysis points out that an ideal gait is one with minimum energy spent during each cycle. The WHLS pattern should be smooth without any extra features. An example shown in FIG. 12 depicts the ZY view (i.e. surge/heave) of a WHLS trace. It is far from being a smooth oval or circle. It has a major feature at locations A that represents a motion of wasted energy. By combining WHLS measurement with frame-by-frame motion analysis, it is possible to identify the cause of this feature and eliminate it. Thus, this approach can be used as an effective and systematic tool to improve one's gait.

Figure 13:
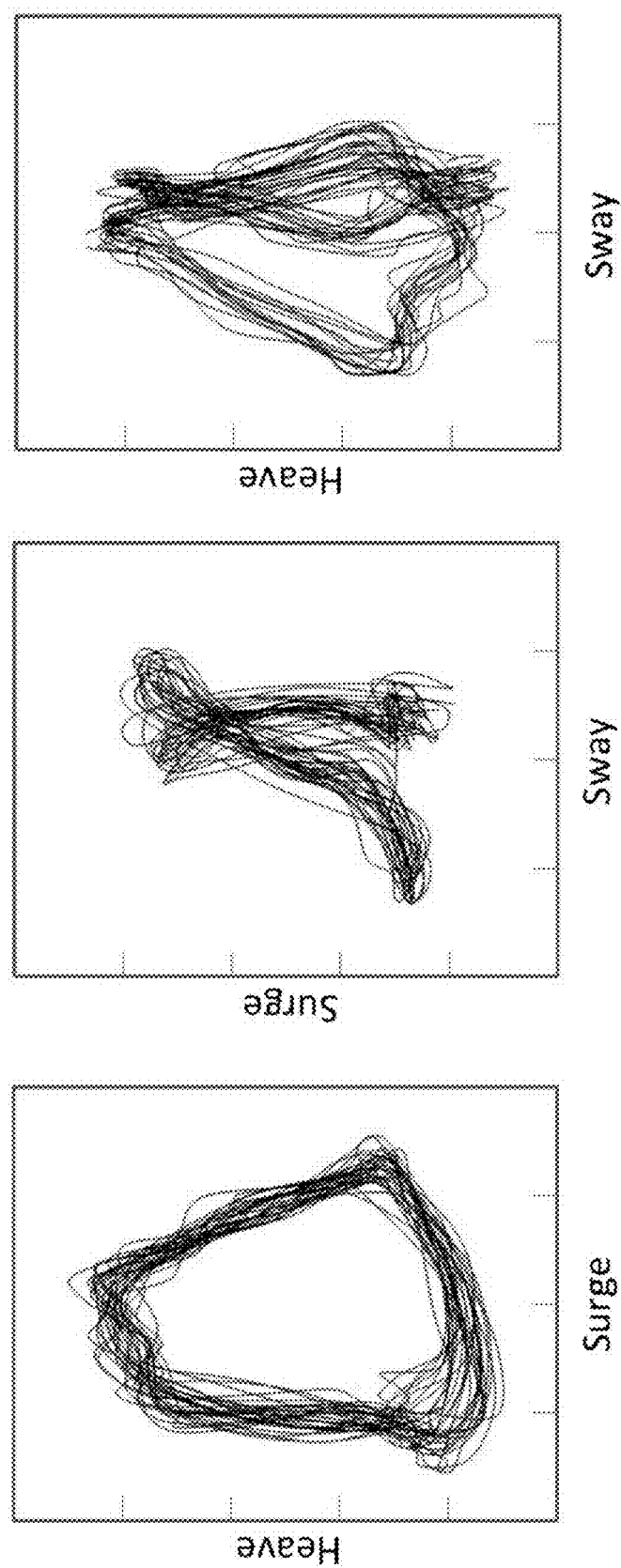
FIG. 13 shows 2D WHLS patterns measured for a dog by placing the accelerometer embedded in a smartphone on its back.

This invention can also be applied to measure the gait for animals. FIG. 13 shows 2D WHLS patterns measured for a dog by placing the accelerometer embedded smartphone on its back. The dog was running on a treadmill at 5.6 km/hr which is much faster than the 2 km/hr speed for human in the WHLS measurement. Due to the anatomic and kinesthetic difference, there are some unique features. First, the sway frequency of a dog is half of the heave and surge frequency, while for human, the frequency of all three movements is the same. Second, the "split fork" pattern seen in many human WHLS's in the Heave/Sway components shows up in dog's gait in the Surge/Sway components. In this particular case, the measurements clearly show that the dog's gait is highly asymmetric and favors toward the right side. Third, the side view of WHLS, or the surge/heave component, shows remarkable consistency with very little variation from stride to stride over a long period of time. The shape is smooth without irregular features found in many human WHLS. This is the most desirable running WHLS. This measurement suggests the usefulness of the invention to measure animal's gait. Applications can be found in selecting and training race horses. This invention can also used by veterinarians in diagnosing kinesthetic problems for sick animals who cannot communicate with verbally.

The present invention has many embodiments of different applications, such as:

To monitor and improve running form for people at all athletic levels with real time monitoring and instruction via Wi-Fi.

To monitor progress of patients in physical rehab program quantitatively with digital and graphical presentation.

To monitor the physical well-being of patients suffering from conditions that can impede the movement.

To monitor the gait of physically handicapped patients and improve prosthetic design.

To record digital evidence for sobriety test.

To improve jogging/walking form in real time via a portable device.

Wearing a portable device (e.g. smart phone with 3 axes accelerometer) on the lower back of the runner (i.e. Center of Mass) to collect acceleration data and running form while exercising.

To calculate the WHLS (Walking, Heaving and Lateral movement Signature) in real time.

To compare the measured WHLS to ideal WHLS and find discrepancy and instruct to make gait correction in real time.

From existing database for ideal running form, to determine the solution to correct this discrepancy.

To give an audio command to the runner to correct his/her running form.

To provide scientific bases for the selecting thoroughbred race horse.

Record and use as biometric identification.

Design of new footwear.

Design of new backpacks and other forms of luggage.

To design exercise equipment that will yield the highest efficiency and least damage to body.

To develop software package so it can be used as a stand-alone gait monitoring with just a hand held device.

To help customer to select the best fitting and most comfortable footwear.

To facilitate veterinarians to pinpoint kinesthetic problems for animals despite that the absence of verbal communication between the patient and the doctor.

INDUSTRIAL APPLICABILITY

The present invention discloses a method of gait measurement using tri-axial accelerometer/gyro in mobile devices. In particular, the present invention relates to a method of gait measurement using tri-axial accelerometer/gyro in mobile devices for monitoring and improving the physical movement of a moving subject.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extend. All publications recited herein are hereby incorporated by reference in their entirety.

What is claimed is:

1. A method for real-time measurement of gait imperfection in a human subject, the method comprising:
    placing a mobile communication device against a lower back of said human subject, wherein the mobile communication device is equipped with a tri-axial accelerometer or a gyro;
    measuring in real-time under a sampling frequency, by the mobile communication device, walking, heaving and lateral movements of said human subject, wherein the sample frequency is determined based on a movement pattern of the human subject;
    constructing in real-time a signature of said subject based on movements measured by the mobile communication device;
    wherein the signature is a three-dimensional trajectory in orthogonal directions of said subject's center of gravity's acceleration trajectory, the three-dimensional trajectory comprising direction and magnitude of acceleration components of the movements, and phase relationships between the acceleration components of the movements in different directions;
    constructing in real-time a power level ($W_{ij}$) dispensed by said subject to keep balance during motion quantitatively based on said signature by computing a summation of forces associated with individual segments along a trajectory of the center of gravity of said subject divided by a total measurement time; and
    generating an output to indicate the gait imperfection in the human subject, wherein the generated output comprises the constructed signature and the constructed power level.

2. The method according to claim 1, wherein said signature is used in monitoring, diagnosing and improving the movement performance of said human subject.

3. The method according to claim 1, wherein said signature is used in monitoring the progress of physical rehabilitation or physical well-being or both of said human subject via the movement of said human subject.

4. The method according to claim 1, wherein said signature is used in the designing or fitting of prosthesis or both for said human subject.

5. The method according to claim 1, wherein said signature is used as a biometric identifier of said human subject.

6. The method according to claim 1, wherein said signature is used as an indicator for physical impairment analysis of said human subject.

7. The method according to claim 1, wherein said signature is used as an identifier for selecting human subjects with better form of movement.

8. The method according to claim 1, wherein said signature is used in designing of footwear for said human subject.

9. The method according to claim 1, wherein said signature is used as an indicator in the fitting and selecting footwear for said human subject.

10. The method according to claim 1, wherein said signature is used in the designing of an exercise equipment for said human subject.

11. The method according to claim 1, wherein said signature is used in the designing of backpacks and other forms of carry luggage for said human subject.

12. The method according to claim 1, wherein said sampling frequency is 100 Hz or higher.

13. The method according to claim 1, wherein sensitivity of said tri-axial accelerometer or gyro is approximately 0.003 g.

14. The method according to claim 1, further comprising:
    formulating a reference table of a plurality of said power levels of a plurality of human subjects with a plurality of fitness levels under a plurality of conditions;
    measuring gait imperfection of said human subject based on the obtained power level of said human subject in reference to said reference table; and correcting said gait imperfection of said human subject through external activity.

15. An apparatus for real-time measurement of gait imperfection in a human subject comprising:
    a mobile communication device having a tri-axial accelerometer or a gyro placed against a lower back of said human subject and configured to measure in real-time under a sampling frequency walking, heaving and lateral movements of said human subject, wherein the sample frequency is determined based on a movement pattern of the human subject;
    a computer processor configured to:
        constructing in real-time a signature of said subject based on movements measured by the mobile communication device;
    wherein the signature is a three-dimensional trajectory in orthogonal directions of said human subject's center of gravity's acceleration trajectory, the three-dimensional trajectory comprising direction and magnitude of acceleration components of the movements, and phase relationship between the acceleration components of the movements in different directions; and
    constructing in real-time a power level dispensed by said human subject to keep balance during motion quantitatively based on said signature by computing a summation of forces associated with individual segments along a trajectory of the center of gravity of said human subject divided by a total measurement time; and
    generating an output to indicate the gait imperfection in the human subject, wherein the generated output comprises the constructed signature and the constructed power level.

* * * * *